United States Patent
Bennett et al.

(10) Patent No.: US 9,144,796 B1
(45) Date of Patent: Sep. 29, 2015

(54) METHOD OF APPLYING WASHCOAT TO MONOLITHIC SUBSTRATE

(75) Inventors: Christopher John Bennett, Exton, PA (US); John P. Coll, Barto, PA (US); Debnath De, Malvern, PA (US); Andrea Hawkins, Reading (GB); Wendy Manning, Barto, PA (US)

(73) Assignee: Johnson Matthey Public Limited Company, London (GB)

( * ) Notice: Subject to any disclaimer, the term of this patent is extended or adjusted under 35 U.S.C. 154(b) by 1245 days.

(21) Appl. No.: 12/752,753

(22) Filed: Apr. 1, 2010

Related U.S. Application Data (60) Provisional application No. 61/165,540, filed on Apr. 1, 2009.

(51) Int. Cl.
    *B01J 37/00* (2006.01)
    *B01J 37/02* (2006.01)
    *B05D 7/22* (2006.01)

(52) U.S. Cl.
    CPC .......... *B01J 37/0215* (2013.01); *B01J 37/0219* (2013.01); *B01J 37/0244* (2013.01); *B05D 7/22* (2013.01); *Y10S 502/514* (2013.01); *Y10S 502/52719* (2013.01)

(58) Field of Classification Search
    USPC ................................ 427/230–239; 106/162.1
    See application file for complete search history.

(56) References Cited

U.S. PATENT DOCUMENTS

| | | | |
|---|---|---|---|
| 3,302,410 A | 2/1967 | McLean et al. | |
| 3,846,442 A | 11/1974 | Habermeier et al. | |
| 4,465,810 A | 8/1984 | Toepker et al. | |
| 4,534,795 A | 8/1985 | Lewis et al. | |
| 4,609,563 A * | 9/1986 | Shimrock et al. | 427/8 |
| 4,783,503 A | 11/1988 | Gergen et al. | |
| 5,449,732 A | 9/1995 | Smith et al. | |
| 5,696,072 A * | 12/1997 | Nercissiantz et al. | 510/206 |
| 5,698,303 A | 12/1997 | Caldwell | |
| 5,866,210 A * | 2/1999 | Rosynsky et al. | 427/294 |
| 5,869,172 A | 2/1999 | Caldwell | |
| 5,953,832 A * | 9/1999 | Rosynsky et al. | 34/403 |
| 6,172,134 B1 | 1/2001 | Cooke | |
| 6,271,377 B1 | 8/2001 | Galbo et al. | |
| 6,325,884 B1 | 12/2001 | Karam | |
| 6,478,874 B1 * | 11/2002 | Rosynsky et al. | 118/63 |
| 6,652,915 B1 | 11/2003 | Baumgart et al. | |
| 7,241,410 B2 | 7/2007 | Stiattesi | |
| 7,521,087 B2 * | 4/2009 | Rosynsky et al. | 427/231 |
| 7,678,416 B2 * | 3/2010 | Suzuki et al. | 427/230 |
| 7,837,890 B2 | 11/2010 | Stockum et al. | |
| 8,088,297 B2 | 1/2012 | Kuebelbeck et al. | |
| 8,574,670 B2 * | 11/2013 | Liu et al. | 427/230 |
| 8,703,236 B2 * | 4/2014 | Chandler et al. | 427/238 |
| 8,863,685 B2 * | 10/2014 | Mori et al. | 118/66 |
| 2003/0072694 A1 | 4/2003 | Hodgson et al. | |
| 2004/0002559 A1 | 1/2004 | Troutman et al. | |
| 2006/0197056 A1 | 9/2006 | Martin | |
| 2007/0129528 A1 | 6/2007 | Huang et al. | |
| 2007/0179242 A1 | 8/2007 | Landon | |
| 2007/0256736 A1 * | 11/2007 | Tonkovich et al. | 137/92 |
| 2008/0069949 A1 | 3/2008 | Glockner et al. | |
| 2008/0145625 A1 | 6/2008 | Schumacher et al. | |
| 2008/0262144 A1 | 10/2008 | Glockner et al. | |
| 2009/0035506 A1 | 2/2009 | Pind et al. | |
| 2009/0160091 A1 | 6/2009 | Zhu et al. | |
| 2009/0227732 A1 | 9/2009 | Glockner et al. | |
| 2010/0208429 A1 | 8/2010 | Zhang et al. | |
| 2010/0233146 A1 | 9/2010 | McDaniel | |
| 2011/0042004 A1 | 2/2011 | Schubert et al. | |
| 2011/0054042 A1 * | 3/2011 | Wu et al. | 514/772.4 |
| 2012/0129995 A1 | 5/2012 | Pirrung et al. | |
| 2012/0251832 A1 | 10/2012 | Huang et al. | |
| 2013/0281580 A1 | 10/2013 | Malofsky et al. | |
| 2013/0309448 A1 | 11/2013 | Striegler et al. | |

FOREIGN PATENT DOCUMENTS

| | | |
|---|---|---|
| DE | 10303651 A1 | 8/2004 |
| EP | 1 057 519 B1 | 12/2000 |
| EP | 1 276 549 B1 | 1/2003 |
| GB | 765562 A | 1/1957 |
| GB | 879243 A | 7/1958 |
| GB | 907769 A | 10/1962 |
| GB | 922924 A | 4/1963 |
| GB | 998240 A | 7/1965 |
| GB | 2385856 A | 9/2003 |
| WO | 9105085 | 4/1991 |
| WO | 9636758 | 11/1996 |
| WO | 9636761 | 11/1996 |
| WO | 9948988 | 9/1999 |
| WO | WO-99/47260 A1 | 9/1999 |
| WO | 0020336 | 4/2000 |
| WO | 0037737 | 6/2000 |
| WO | 0144452 A1 | 6/2001 |
| WO | 02064877 A2 | 8/2002 |
| WO | 03085039 A1 | 10/2003 |
| WO | 2004046214 A2 | 6/2004 |
| WO | 2006002935 A1 | 1/2006 |
| WO | 2006084523 A1 | 8/2006 |

(Continued)

*Primary Examiner* — William Phillip Fletcher, III
(74) *Attorney, Agent, or Firm* — Kevin M. Caroll (57) ABSTRACT

A method of coating substrate monoliths is disclosed. The method comprises locating a containment means on top of the first end face of the monolith; and dosing a predetermined quantity of washcoat composition comprising a liquid phase, at least one polysaccharide rheology modifier and at least one of (i) a suspension of metal oxide particles into the containment means; and (ii) at least one metal salt solute in the liquid phase. The locating step may occur before or after the dosing step. Pressure is applied to the washcoat composition to generate shear stress and to transfer an entirety of washcoat composition into the channels of the monolith by plug flow. Substantially all of the predetermined quantity is retained within the monolith. The part-coated monolith is then rotated so that the second end face is located at the top, and the first three steps are repeated without drying the part-coated monolith.

6 Claims, 3 Drawing Sheets

(56) References Cited

FOREIGN PATENT DOCUMENTS

| WO | 2006094849 | A1 | 9/2006 |
| WO | 2007077057 | A1 | 7/2007 |
| WO | 2008154011 | A1 | 12/2008 |
| WO | 2011005214 | A1 | 1/2011 |
| WO | 2013059479 | A2 | 4/2013 |

* cited by examiner

METHOD OF APPLYING WASHCOAT TO MONOLITHIC SUBSTRATE

CROSS-REFERENCE TO RELATED APPLICATION

This application claims priority from U.S. Provisional Application No. 61/165,540, filed Apr. 1, 2009, which is incorporated herein by reference in its entirety for all purposes.

FIELD OF THE INVENTION

The present invention relates to a washcoat composition, in particular a washcoat composition for coating a substrate monolith, and to a method of coating a substrate monolith with such washcoat composition.

BACKGROUND OF THE INVENTION

WO 99/47260 (the entire contents of which is incorporated herein by reference) discloses an apparatus for coating a substrate monolith comprising a plurality of substantially parallel channels extending from a first end face to a second end face thereof, which apparatus comprising means for dosing a pre-determined quantity of a liquid component, such quantity being such that may be substantially wholly retained within a substrate monolith to be coated, liquid component containment means locatable on the top of the substrate monolith to receive said quantity of liquid component, and pressure means such as over-pressure or a vacuum for transferring the liquid component from the containment means into at least a portion of the substrate monolith. An important characteristic of the disclosed apparatus and method is that substantially all of the liquid is retained within the substrate monolith, ensuring an even distribution in the desired pattern, and ensuring that there is no significant excess liquid requiring recycling. This feature is particularly important to reduce or prevent losses of the liquid component, and any precious metals contained therein. In a preferred embodiment wherein substantially all of the liquid component is retained within the substrate monolith, the method may be used to part-coat the substrate monolith in a first axial direction from one end face, before the part-coated substrate monolith is turned and the remainder of the substrate monolith is coated from the opposite end face in the same axial direction.

The description mentions that for certain coating components, the rheology of the liquid component may be such that it does not begin to enter the cells of the substrate monolith until pressure or vacuum is applied. In particular, the apparatus and method of the invention may provide plug flow of the dispensed quantity of liquid into the support.

"Rheology" may be defined as a material's response to a stress applied on the material during production, processing and/or application. Rheology measures the change in viscosity of a substance under changing shear rates, or a change in viscosity over time, at a constant shear rate.

SUMMARY OF THE INVENTION

We have now identified a family of rheology modifiers for use in the apparatus and the method disclosed in WO 99/47260, which provides a range of particular advantages in use.

According to a first aspect, there is provided a washcoat composition comprising a liquid phase, at least one polysaccharide rheology modifier and either one or both of (a) suspended metal oxide particles and (b) at least one metal salt solute in the liquid phase, wherein the rheology of the washcoat composition is pseudoplastic.

BRIEF DESCRIPTION OF THE DRAWING

In order that the invention may be more fully understood, the following Examples are provided by way of illustration only and with reference to the accompanying drawings, in which.

DETAILED DESCRIPTION OF THE INVENTION

It will be appreciated that the art sometimes refers to a "washcoat" as a "slurry" comprising metal oxide particles. For the avoidance of any doubt "washcoat composition" herein is used to refer to either compositions containing metal oxide particles or, in the alternative, compositions that do not contain metal oxide particles.

As used herein, the term "liquid phase" is meant to include liquids, solutions, suspensions, colloids, sols, emulsions, and gels.

The rheology, or flow behaviour, of a material may be classified as Newtonian and non-Newtonian. Newtonian flow describes a material that exhibits no change in viscosity with increasing shear rate. A classical example of a compound with Newtonian behaviour is water. Non-Newtonian flow includes pseudoplastic, thixotropic or dilatant flow, based on the measured response of the material to a known shear rate, compared to classical models.

Pseudoplastic flow describes a system that exhibits a reduction in viscosity with increasing shear rate. The viscosity will recover as the shear is removed; though it may not follow the same viscosity profile as exhibited with increasing shear. This type of flow is also referred to as "shear thinning". In contrast the viscosity characteristics of a pseudoplastic material, the viscosity of a thixotropic fluid decreases over time at a constant shear rate. Rheology modifiers useful in the present invention provide the washcoat with pseudoplastic properties although the modifiers may also impart thixotropic properties under certain conditions.

It can be seen that pseudoplastic flow is a particular advantage in the method disclosed in WO 99/47260 because, when the pressure means is actuated it generates a shear stress in a pseudoplastic gel-like washcoat composition deposited in the containment means on top of an upper face of the substrate monolith, which pressure means reduces the viscosity of the washcoat composition and enables it to be drawn into the channels of the monolith substrate and coating the channels by plug flow. The quantity of washcoat composition is selected so that when plug flow breaks down, the washcoat composition is substantially wholly retained within the channels of the substrate monolith. Moreover, since the shear stress is substantially removed when plug flow breaks down and/or when the pressure means is deactivated, the pseudo-plastic nature of the washcoat composition means that it returns to a gel-like consistency, thus holding the washcoat composition where it has been coated in the channels of the substrate monolith.

The use of rheology modifiers in compositions comprising a liquid phase and a suspension of particulate metal oxides is known in printing inks. However, printer inks typically exhibit rheopectic-type behaviour—that is, they become more viscous when subjected to shear stress (e.g., shaking). Moreover, such alternative applications may be further distinguished by any one or more of a number of the following characteristics of a washcoat composition. For example, depending on the application of the substrate monolith e.g. a filter or a flow-through substrate monolith for diesel or gasoline applications, the metal oxide particles may have a D50 of 0.1-6.0 μm, such as 3.0-5.0 μm or 0.1-2.0 μm; or a D90 of <15.0 μm, such as less than 13.0 μm, e.g. less than 12.0 μm or less than 5.0 μm; a solids content of 3-40 wt %, such as 15-40%, 30-40% or 3-15%; the pH of the washcoat is acidic, i.e. <pH 7, such as <pH 6.0, <pH 5.0, <pH 4.0, <pH 3.0, <pH 2.0, <pH 1.5 or <pH 1.0; or the liquid phase comprises water, e.g. 90% water, such as >95% water or >98% water—in other words, preferred rheology modifiers are tolerant to low pH; they will still gel the composition. Metal oxide particles can be measured using a suitable instrument, e.g. a Malvern LS2000 particle sizer using the Mie optical model.

Another aspect of pH tolerance is that preferred rheology modifiers for use in the present invention are resistant to multivalent ions at such low pH. Accordingly, the preferred rheology modifiers are resistant (they will still gel the composition) to one or more multivalent cations of any of the metal salts listed hereinbelow, including: $Pt^{2+}$, $Pt^{4+}$, $Pt^{6+}$, $Pd^{2+}$, $Rh^{3+}$, $Cu^{2+}$, $Fe^{2+}$, $Fe^{3+}$, $Ni^{2+}$, $Ni^{3+}$, $Co^{2+}$, $Co^{3+}$, $Ce^{4+}$, $Zr^{4+}$, $Y^{3+}$, $Pr^{3+}$, $La^{3+}$, $Mg^{2+}$, $Ca^{2+}$, $Sr^{2+}$, $Ba^{2+}$, molybdates such as $Mo_7O_{24}^{6-}$ and $Mo_8O_{26}^{4-}$ and tungstate ($WO_4^{2-}$).

The metal oxide for use in the washcoat composition may be selected from the group consisting essentially of alumina, ceria, zirconia, ceria-zirconia, silica, silica-alumina, titania, a zeolite or mixtures of any two or more thereof. The definition "consisting essentially" anticipates the presence of minor amounts of promoters e.g. barium and/or stabilisers, e.g. lanthanum stabilised alumina, that may affect the washcoat composition, but do not function as a metal catalyst per se.

Preferably, each metal in the metal salt of the washcoat composition according to the invention can be selected from the group consisting of Group IA (e.g. potassium, caesium), Group IB (e.g. copper, silver, gold), Group IIA (e.g. magnesium, calcium, strontium, barium), Group IIIB (e.g. yttrium, lanthanides such as cerium and praseodymium), Group IVB (e.g. zirconium), Group VB (e.g. vanadium), Group VIB (e.g. molybdenum, tungsten), Group VIIB (e.g. manganese) and Group VIII (e.g. iron, ruthenium, nickel, palladium, rhodium, platinum, palladium).

In one embodiment, each metal in the metal salt is a transition metal, wherein the transition metal can be a precious metal (i.e. Au, Ag, Pt, Pd, Rh, Ir, Os, Ru etc.), Cu, Fe, Mn, Ce, Zr, W or V. In a preferred embodiment, each precious metal is a platinum group metal, i.e. Pt, Pd, Rh, Ir, Os, Ru etc. Suitable combinations of platinum group metals, depending on the application, include Pt/Rh for $NO_x$ absorbers and Pt/Pd for diesel oxidation catalysts (DOCs).

According to an embodiment of the invention, the invention extends to the possibility of pre-fixing one or more of the abovementioned metals in the metal salts on the metal oxide particles prior to forming the washcoat composition. Pre-fixed metals may be present as elemental metal or as a metal compound, such as an oxide. Methods of pre-fixing include impregnating the metal oxide particles with a suitable salt solution followed by drying a calcining (firing) step. It is also envisaged that the washcoat composition can comprise metal pre-fixed on the metal oxide particles and at least one metal salt solute in the liquid phase.

It will be appreciated that the coated substrate monoliths can be used in a wide range of applications, including treating industrial effluent and "off-gas" and for treating emissions from stationary source and mobile applications such as diesel or gasoline engines and gas turbines. Accordingly, the substrate monoliths and the components in the washcoat components may be selected dependent on the desired application, e.g. selective catalytic reduction using nitrogenous reductants or hydrocarbon reductants, $NO_x$ absorption, oxidation such as diesel oxidation, three-way catalysis etc.

The rheology modifier for use in the present invention preferably comprises one or more polysaccharide and can be a naturally occurring product or derived from a naturally occurring product, or a synthetic product. It can be ionic, such as anionic, or non-ionic.

In one embodiment, the rheology modifier comprises at least one polysaccharide selected from the group consisting of a galactomannan gum, xanthan gum, curdlan, Schizophyllan, Scleroglucan, Diutan gum, Welan gum and mixtures of any two or more thereof. For embodiments wherein the washcoat requires low pH and high temperature stability, the rheology modifier preferably comprises Scleroglucan and/or Schizophyllan, with Scleroglucan being particularly preferred.

Galactomannans are naturally occurring polysaccharides consisting of a mannose backbone with galactose side groups (more specifically, a (1-4)-linked beta-D-mannopyranose backbone with branchpoints from their 6-positions linked to alpha-D-galactose, i.e. 1-6-linked alpha-D-galactopyranose) obtainable from the beans of certain plants. In order of increasing number of mannose:galactose, galactomannans include fenugreek gum (mannose:galactose ~1:1), guar gum (mannose:galactose ~2:1), tara gum (mannose:galactose ~3:1) and locust bean gum or carob gum (mannose:galactose ~4:1).

The backbone of the polysaccharide chain of xanthan gum consists of two β-D-glucose units linked through the 1 and 4 positions. The side chain consists of two mannose and one glucuronic acid, so the chain consists of repeats of five sugar units. Dissolved xanthan chains also assume a rod-like double helix structure. It is produced by a process involving fermentation of glucose or sucrose by the *Xanthomonas campestris* bacterium.

Curdlan is naturally occurring polysaccharide produced by *Agrobacterium* biobar. It consists of Beta-1,3-glucan, a high molecular weight polymer.

Schizophyllan is a neutral, extracellular polysaccharide produced by the fungus *Schizophyllan commune*, consisting of a 1,3-β-D-linked backbone of glucose residues with 1,6-β-D-glucosyl side groups.

Scleroglucan is a water-soluble natural non-ionic polymer produced by the fermentation of the filamentous fungi *sclerotium rofsii*. The chemical structure consists of beta 1,3-D-glucose residues with one beta-1,6-D-glucose side chain every three main residues. Dissolved scleroglucan chains also assume a rod-like triple helical structure, in which the glucose residues sit on the outside.

Welan gum is an anionic microbial polysaccharide produced by a species of *Alcaligenes*. The structure is based on repeating glucose, rhamnose and glucuronic acid units but with a single side chain of either an α-L-rhamnopyranosyl or an α-L-mannopyranosyl unit linked (1-3) to the 4-O-substituted β-D-glucopyranosyl unit in the backbone.

Diutan gum is a biopolymer very similar to Welan gum. Welan gum and diutan gum also assume the rod-like triple helical configuration seen in scleroglucan.

Scleroglucan, welan gum and diutan gum have a number of interesting properties that make them potentially very useful to the methods disclosed, e.g. in WO 99/47260. These include that they are relatively stable, e.g. relative to xanthan gums, in low pH, e.g. <pH 3.0, <pH 2.0, <pH 1.5 or <pH 1.0; their viscosity increases with temperature; and their viscosity increases with time in the absence of applied shear stress. For example, we have seen that for 1-1.5% solution of polysaccharide rheology modifiers that assume a rod-like triple helical structure when dissolved in water, viscosity increases by over 100% between 70 and 100° C., as measured on a Brookfield viscometer at 10° C. increments. It will be appreciated that in using a Brookfield viscometer, absolute viscosity readings may vary depending on what spindle number and/or conditions (most significantly spindle revolutions per minute (rpm)) are employed. However, regardless of what spindle or conditions are used, the trend of viscosity against temperature will be consistent for a given washcoat composition.

In an alternative embodiment, the polysaccharide rheology modifier is a starch, a cellulose or an alginate or is derived from a starch, a cellulose (i.e. cellulosic) or an alginate, though these rheology modifiers do not share all of the properties of scleroglucan, welan gum and diutan gum, e.g. hydroxyethyl cellulose may degrade on heating even at neutral or basic pH.

The cellulosic rheology modifier may be selected from the group consisting of carboxymethyl cellulose, hydroxymethyl cellulose, hydroxyethyl cellulose, methyl cellulose, methyl hydroxyethyl cellulose, methyl hydroxypropyl cellulose and ethyl hydroxyethyl cellulose.

The polysaccharide rheology modifier may be an associative rheology modifier, cellulosic examples of which include hydrophobically modified hydroxyethyl cellulose or hydrophobically modified ethyl hydroxyethyl cellulose. In our investigations, however, we have noticed that certain cellulosic rheology modifiers, such a hydroxy methyl cellulose, behave differently in a washcoat composition than in water. For example, we have seen that hydroxy methyl cellulose becomes associative in a washcoat composition, e.g. at acid pH, but not in deionised water. This is particularly surprising since hydroxy methyl cellulose is generally not regarded as associative.

It is possible according to the invention to use a single rheology modifier as defined herein, or a mixture or any two or more thereof. For example, in one embodiment, the at least one rheology modifier can be a mixture of guar gum and xanthan gum.

Rheology modifiers are generally present in the washcoat composition according to the invention at up to 5.0 wt % per volume, such as up to 4.0 wt % per volume, up to 3.0 wt % per volume, 2.0 wt % per volume, 1.5 wt % per volume and 1.0 wt % per volume.

As defined herein, "substrate monolith", "substrate" or "monolith" is a structure comprising a plurality of generally parallel channels extending in a generally axial direction through at least part of the structure and, in certain preferred embodiments, is a ceramic or metal honeycomb. The channels can have any cross sectional shape e.g. square, triangular etc. The structure can be the so-called "flow through" arrangement, where both inlet and outlet ends of the channels are open to fluid flow or the structure can be a filter. Various filter arrangements are known, including the so-called wall flow filter, wherein each channel has a plug at one end and the opposite end is open, with any pair of adjacent channels having plugs at opposite channel ends. The term "filter" herein, also includes partial filters, such as those disclosed in EP 1276549 and EP 1057519 (the entire contents of both documents being incorporated herein by reference).

According to a further aspect, the invention provides the use of at least one polysaccharide rheology modifier (as described hereinabove) in the manufacture of a rheologically pseudoplastic washcoat composition for coating a substrate monolith, wherein the washcoat composition comprises a liquid phase and either one or both of (a) suspended metal oxide particles and (b) at least one metal salt solute in the liquid phase, wherein the rheology of the washcoat composition is pseudoplastic.

An aspect of the method disclosed in WO 99/47260 is that each coating step may need to be followed immediately by a drying step and optionally also by a firing (i.e. calcining) step. The use of the polysaccharide rheology modifiers disclosed herein can reduce the number of process steps involved in obtaining the final coated substrate monolith, i.e. they enable a substrate monolith to be part-coated in a first axial direction from one end face, before the part-coated substrate monolith is turned and the remainder of the substrate monolith is coated from the opposite end face in the same axial direction without a drying step between a first washcoat application and a second washcoat application.

The characteristics of rheology modifiers comprising polysaccharide chains that assume rod-like double and particularly triple helices when dissolved—such as scelroglucan, welan gum and diutan gum—are particularly useful in the method disclosed in WO 99/47260. Using these rheology modifiers in particular, it is possible to coat a substrate monolith from one end by application of shear stress using the pressure means and to turn the substrate monolith without first drying the first part-coating before the substrate monolith is coated from the opposite end face. That is, pressure means is applied across an undried first part-coating. One feature of the selected rheology modifiers that facilitates this is that they make the washcoat strongly pseudoplastic, i.e. they can increase in washcoat viscosity rapidly producing a strong gelled-structure (due to triple helical structures of thickeners) with time upon the cessation of the applied shear stress.

Moreover, the use of the above rheology modifiers enables a second washcoat layer to be applied over the dried first washcoat layer, i.e. it may not be necessary first to fire (calcine) the first washcoat layer before overlaying the first washcoat layer with a second washcoat layer. One reason for this is that the drying step sufficiently increases the viscosity of the washcoat composition of the first layer.

The feature that the selected polysaccharide rheology modifiers, e.g. scleroglucan, welan gum and diutan gum, are stable in low pH is also an advantage for washcoating systems that require acid pH, e.g. to impregnate anionic platinum group metal salts onto acidic metal oxide particles, e.g. alumina, silica-alumina and titania. For example, we have seen that relatively low pH washcoat compositions (e.g. less than pH 2.0) containing polysaccharide rheology modifiers that assume a rod-like triple helical structure when dissolved in water retain their viscosity (tested on a Brookfield viscometer) when stored for over two months. This was confirmed for two washcoat compositions, one comprising metal salts (Ce:Zr nitrate) and the other comprising a slurry of metal oxide particles (alumina). It was also observed, that these preferred rheology modifiers are resistant to multivalent cations (such as $Ce^{4+}$ and $Zr^{4+}$) at the low pHs tested.

Accordingly, the use of polysaccharide rheology modifiers in general, and these selected rheology modifiers in particular, is advantageous in that they can reduce substantially the number of process steps necessary to obtain a coated substrate monolith.

According to another aspect of the invention, provided is a method for coating a substrate monolith having a plurality of channels and having a first end, wherein said first end comprises a plurality of channel openings, comprising: (a) contacting a predetermined quantity of a rheologically pseudoplastic washcoat with said first end, wherein said washcoat comprises a liquid phase, a polysaccharide rheological modifier, and either one or both of (i) suspended metal oxide particles and (ii) at least one metal salt solute in the liquid phase; (b) applying a vacuum and/or positive pressure to said washcoat, wherein said applying said vacuum and/or positive pressure decreases the viscosity of the washcoat; (c) coating at least a portion of said channels with said washcoat; and (d) removing said vacuum and/or positive pressure from said washcoat. In a particularly preferred embodiment, steps (a), (b), (c), and (d) of this method are performed in the order described above.

According to another aspect, the invention provides a method of coating a substrate monolith comprising a first end face and a second end face and a plurality of substantially parallel channels extending from the first end face to the second end face with a washcoat composition, which method comprising the steps of:

(a) locating a containment means on top of the first end face of the substrate monolith;

(b) dosing a predetermined quantity of a rheologically pseudoplastic washcoat composition comprising a liquid phase, at least one polysaccharide rheology modifier and either one or both of (i) and (ii), wherein (i) is a suspension of metal oxide particles; and (ii) is at least one metal salt solute in the liquid phase into the containment means, and wherein the order of steps (a) and (b) is (a) then (b) or (b) then (a);

(c) applying pressure to the washcoat composition thereby to generate a shear stress in the washcoat composition and to transfer an entirety of the washcoat composition into the channels of the substrate monolith by plug flow, wherein the predetermined quantity of the washcoat composition is such that substantially all of the predetermined quantity of the washcoat composition is retained within the substrate monolith; and (d) rotating a part-coated substrate monolith resulting from step (c) so that the second end face is located at the top; and (e) repeating steps (a) to (c) inclusive without drying the part-coated substrate monolith. It will be appreciated that this method is based on the method disclosed in WO 99/47260 (the entire contents of which is incorporated herein by reference).

According to one method according to the invention, the product of step (e) comprises a substrate monolith coated substantially uniformly with a first layer of the washcoat composition.

The product of step (e) can be subjected to a drying step following which it can be fired (calcined) or alternatively the dried product of step (e) can be coated with a second washcoat layer by repeating steps (a) to (e) inclusive before the two layer product can be fired (calcined).

In embodiments, the washcoat composition comprises a platinum group metal, which can be present as a salt solution or pre-fixed to the metal oxide particles.

Of particular application in this method are polysaccharide rheology modifiers that assume a rod-like triple helical structure when dissolved in water, e.g. Scleroglucan, Diutan gum or Welan gum, for reasons explained hereinabove.

The method according to the invention provides a number of very useful advantages where expensive precious metals are used. These include the more rigorous control of precious metals within the method, reducing losses. For example, the present invention allows washcoat compositions comprising precious metal salts to be applied as a separate step to a washcoat layer(s) containing metal oxide particles that has been laid down in previous step, rather than combining precious metal salts and metal oxide particles in the same washcoat composition (although this is still possible according to the present invention). An advantage is that washcoat compositions comprising precious metal salts and no metal oxide particles are more easily analysed, e.g. using Inductively Coupled Plasma Emission Spectroscopy (ICP-ES) using commercially available standards for solutions, than washcoat compositions comprising precious metal salts and metal oxide particles ("slurries") where e.g. X-Ray Fluorescence (XRF) can be used, which requires the preparation of "homemade" standards for slurries.

Secondly, since a precious metal application step can be separated from a step of coating the monolith substrate with a washcoat composition containing metal oxide particles, a problem of flushing lines to recover precious metals when the washcoat composition is changed, e.g. from a rhodium containing washcoat composition to a palladium-containing washcoat composition, can be reduced or avoided. There is an economic benefit in that this reduces the amount of time during which production apparatus is inactive while the lines are being flushed ("downtime"). Also there is an environmental advantage in that less rinse water is used for line flushing. The method according to the invention reduces or avoids this problem.

Thirdly, since it is possible to batch production of washcoat compositions that do not contain precious metals, less analysis is required to ensure accuracy of precious metal content to meet specification. Thus, there is a further economic benefit in the amount of work required.

EXAMPLE 1

Figure 1:
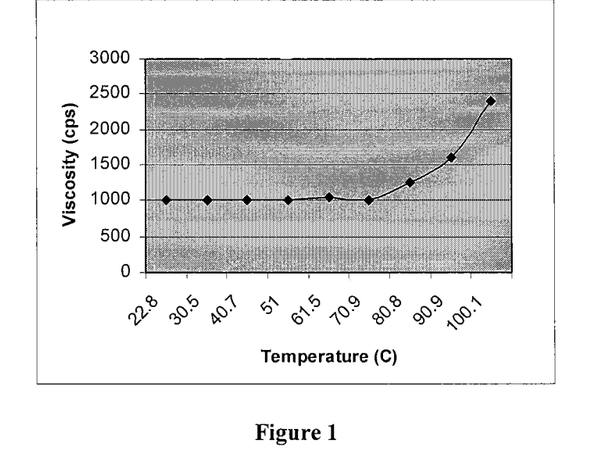
FIG. 1 is a graph in which the viscosity of a solution of scleroglucan in deionised water is plotted against temperature.
Figure 2:
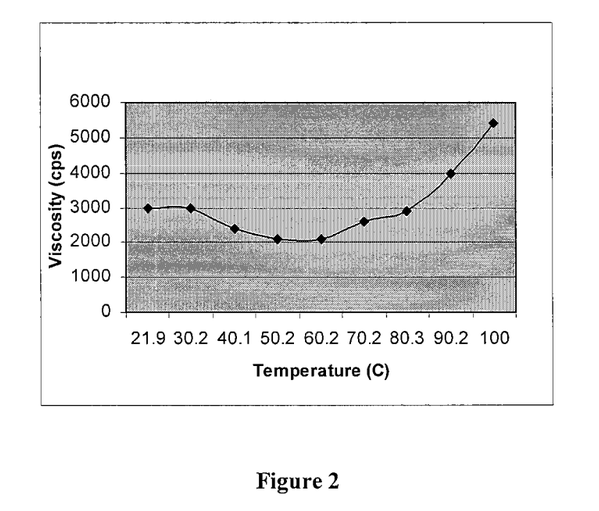
FIG. 2 is a graph in which the viscosity of a solution of guar gum in deionised water is plotted against temperature.

The viscosities (measured in centipoises or cPs) of solutions of scleroglucan (Actigum CS6 or MMP Clearogel) and guar gum (Viscogum 202) in deionised water (pH 5.0) were determined using a Brookfield Viscometer in 10° C. increments. An illustrative results trend is set out in Tables 1 and 2 and is illustrated in FIGS. 1 and 2.

TABLE 1

| Scleroglucan 1.5%: 3 g in 200 ml deionised water | |
|---|---|
| Temperature, ° C. | Viscosity |
| 22.8 | 1000 |
| 30.5 | 1000 |
| 40.7 | 1000 |
| 51 | 1000 |
| 61.5 | 1050 |

TABLE 1-continued

Scleroglucan 1.5%: 3 g in
200 ml deionised water

| Temperature, ° C. | Viscosity |
| --- | --- |
| 70.9 | 1000 |
| 80.8 | 1250 |
| 90.9 | 1600 |
| 100.1 | 2400 |

TABLE 2

Guar Gum - 1%: 2 g in
200 ml deionised water

| Temperature, ° C. | Viscosity |
| --- | --- |
| 24.6 | 1600 |
| 30.6 | 2400 |
| 41.6 | 2600 |
| 51.2 | 2800 |
| 60.7 | 2700 |
| 70.5 | 2600 |
| 80.8 | 2500 |
| 91.1 | 2500 |
| 24.6 | 1600 |

It can be seen that the viscosity of both these rheology modifiers increases with increasing temperature.

EXAMPLE 2

Figure 3:
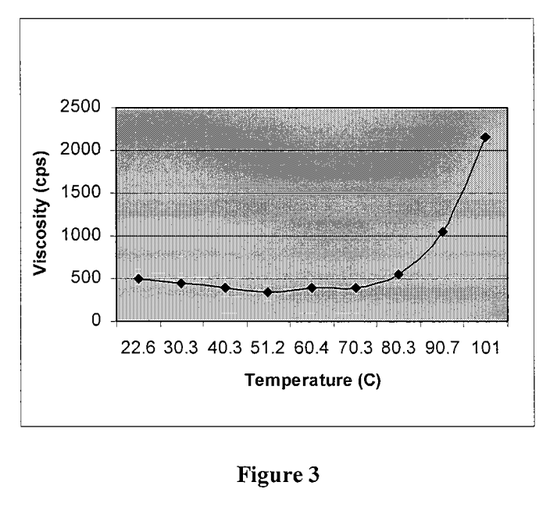
FIG. 3 is a graph in which the viscosity of a washcoat composition comprising a solution of Ce:Zr nitrate and scleroglucan is plotted against temperature.
Figure 4:
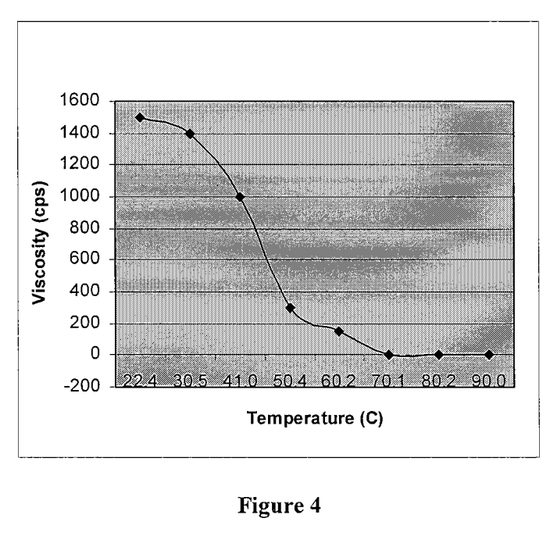
FIG. 4 is a graph in which the viscosity of a washcoat composition comprising a solution of Ce:Zr nitrate and hydroxyethyl cellulose is plotted against temperature.

The viscosity (cPs) of a representative low pH (pH~0.8) washcoat composition comprising a solution of Ce:Zr nitrate and scleroglucan, guar gum or hydroxyethyl cellulose ((Natrosol MR250) no particulate metal oxide) was tested using a Brookfield Viscometer in 10° C. increments. Illustrative results trends for scleroglucan and hydroxyethyl cellulose are set out in Tables 3 and 4. The results are also shown graphically in FIGS. 3 and 4 respectively. Guar gum would not polymerize in the low pH solution.

TABLE 3

Scleroglucan - 1%: 3 g in
300 g Ce:Zr nitrate solution

| Temperature, ° C. | Viscosity |
| --- | --- |
| 24.6 | 1600 |
| 30.6 | 2400 |
| 41.6 | 2600 |
| 51.2 | 2800 |
| 60.7 | 2700 |
| 70.5 | 2600 |
| 80.8 | 2500 |
| 91.1 | 2500 |
| 24.6 | 1600 |

TABLE 4

Hydroxyethyl cellulose - 1%:
3 g in 300 g Ce:Zr nitrate solution

| Temperature, ° C. | Viscosity |
| --- | --- |
| 22.4 | 1500 |
| 30.5 | 1400 |
| 41.0 | 1000 |
| 50.4 | 300 |
| 60.2 | 150 |

TABLE 4-continued

Hydroxyethyl cellulose - 1%:
3 g in 300 g Ce:Zr nitrate solution

| Temperature, ° C. | Viscosity |
| --- | --- |
| 70.1 | 0 |
| 80.2 | 0 |
| 90.0 | 0 |

EXAMPLE 3

Figure 5:
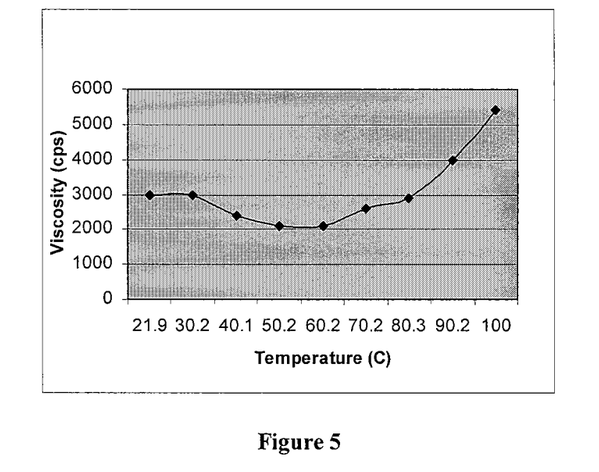
FIG. 5 is a graph in which the which the viscosity of a washcoat composition comprising colloidal alumina and scleroglucan is plotted against temperature.
Figure 6:
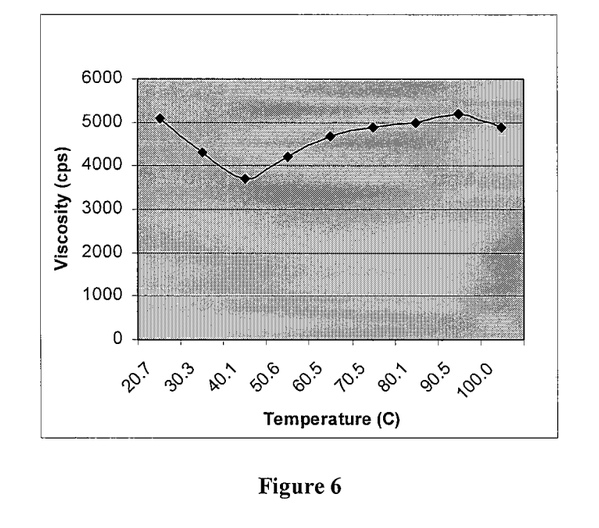
FIG. 6 is a graph in which the viscosity of a washcoat composition comprising colloidal alumina and hydroxyethyl cellulose is plotted against temperature.

The viscosity (cPs) of a representative washcoat composition containing a particulate metal oxide comprising a colloidal alumina doped with citric acid and platinum nitrate at a pH~1.5 was tested using a Brookfield Viscometer in 10° C. increments. The illustrative results trend for scleroglucan and guar gum are set out in Tables 5 and 6 and is also shown in FIGS. 5 and 6.

TABLE 5

Scleroglucan - 0.25%: 1 g in 400 g
colloidal alumina; pH 1.47

| Temperature, ° C. | Viscosity |
| --- | --- |
| 21.9 | 3000 |
| 30.2 | 3000 |
| 40.1 | 2400 |
| 50.2 | 2100 |
| 60.2 | 2100 |
| 70.2 | 2600 |
| 80.3 | 2900 |
| 90.2 | 4000 |
| 100.1 | 5400 |

TABLE 6

Guar gum - 0.125%: 0.5 g in 400 g
colloidal alumina; pH ~1.5

| Temperature, ° C. | Viscosity |
| --- | --- |
| 20.7 | 5100 |
| 30.3 | 4300 |
| 40.1 | 3700 |
| 50.6 | 4200 |
| 60.5 | 4700 |
| 70.5 | 4900 |
| 80.1 | 5000 |
| 90.5 | 5200 |
| 100.0 | 4900 |

It can be seen that scleroglucan and guar gum worked well for thickening washcoat composition containing particulate metal oxide both at room temperature and when heated to typical drying temperatures. The guar gum showed a decrease in viscosity between 30-50° C., but viscosity recovered at higher temperatures. This was observed on two separate samples with two different concentrations of guar gum (results not shown). Scleroglucan also showed a loss in viscosity between 40-60° C. (results not shown). However, when the test was repeated at a higher polymer concentration, the loss in viscosity was much less pronounced.

EXAMPLE 4

To test the pH tolerance of scleroglucan-containing washcoat compositions, samples from Examples 2 and 3 were stored for several weeks at room temperature and their viscosity was determined intermittently, as set out in Tables 7 and 8.

TABLE 7

Scleroglucan - 1%: 3 g in 300 g
Ce:Zr nitrate solution; pH ~0.8

| Date | Viscosity |
|---|---|
| 9$^{th}$ Jul. 2007 | 3200 |
| 12$^{th}$ Jul. 2007 | 4500 |
| 16$^{th}$ Jul. 2007 | 4000 |
| 19$^{th}$ Jul. 2007 | 5000 |
| 24$^{th}$ Jul. 2007 | 5400 |
| 30$^{th}$ Jul. 2007 | 5600 |
| 13$^{th}$ Aug. 2007 | 5700 |
| 12$^{th}$ Sep. 2007 | 6400 |

TABLE 8

Scleroglucan - Scleroglucan - 0.25%:
1 g in 400 g colloidal alumina; pH 1.47

| Date | Viscosity |
|---|---|
| 9$^{th}$ Jul. 2007 | 4700 |
| 12$^{th}$ Jul. 2007 | 5000 |
| 16$^{th}$ Jul. 2007 | 5500 |
| 19$^{th}$ Jul. 2007 | 4500 |
| 24$^{th}$ Jul. 2007 | 4800 |
| 30$^{th}$ Jul. 2007 | 4700 |
| 13$^{th}$ Aug. 2007 | 4900 |
| 12$^{th}$ Sep. 2007 | 5100 |

It can be seen that scleroglucan is a stable rheology modifier in the washcoat composition systems tested.

EXAMPLE 5

Catalysed wall-flow diesel particulate filters having a total length of 12 inches (30.48 cm) were prepared using the method disclosed in WO 99/47260 using the washcoat compositions of Example 2 with the objective of achieving the washcoat component loadings on the catalysed diesel particulate filter set out in Table 9.

TABLE 9

| Position | Particulate Metal Oxide loading (g/in$^3$) | Pt (g/ft$^3$) | Ce (g/ft$^3$) | Zr (g/ft$^3$) | Rheology Modifier % |
|---|---|---|---|---|---|
| 1 | — | | 500 | 500 | Xanthan (Vanzan ®) gum 1% |
| 2 | — | | 500 | 500 | Scleroglucan 1% |
| 3 | 0.35 | 10 | — | — | Xanthan (Vanzan ®) gum 0.5% |
| 4 | 0.35 | 10 | — | — | Scleroglucan 0.5% |
| 5 | 0.35 | 10 | — | — | Guar gum 0.05% |

Positions 1 and 2 of 5 in an automated apparatus were prepared targeting 50% dose lengths measured from the top down. The two samples were then transferred into a dryer and dried for 45 minutes at 100° C. These parts were monitored for solution migration using 3-dimensional X-ray throughout the drying process. During drying, the washcoat composition containing xanthan gum migrated from 50% of the filter length down to approximately 75% of the filter length, whereas the scleroglucan-containing sample at position 2 showed virtually no signs of solution migration during the drying step.

Positions 3-5 were prepared using the colloidal alumina washcoat composition of Example #3. A target dose length of 75% of the total length of the filter was intended (approx. 7 inches or 17.78 cm). Samples were dried at 100° C. for 60 minutes and monitored for washcoat migration.

The filter sample at position #3 using xanthan gum began to migrate on heating to the bottom of the filter in a funnel shaped pattern. The centre of the filter showed a 6 inch (15.24 cm) diameter drainage pattern after 30 minutes of drying. After 60 minutes the drainage increased to a 10 inch (25.4 cm) diameter with a 3 inch (7.62 cm) spot which migrated completely through the filter to the opposite end face creating a 3 inch (7.62 cm) diameter spot with cell blockage.

After 30 minutes of drying the position #4 filter sample the centre of the filter showed one ½ inch of washcoat migration. After 60 minutes the part appeared the same, indicating that the washcoat movement was inhibited by the polymerization of the scleroglucan as the internal temperature increased.

After 30 minutes of drying the guar gum-containing sample at position #5, the centre of the filter showed 1 inch (2.54 cm) of washcoat migration. After 60 minutes the washcoat had moved to 8.5 inch (21.59 cm) down the length of the part.

The position #1 sample showed poor thermal stability: gelled solution migration was uncontrolled after the filter temperature exceeded 40° C.

The position #2 sample using scleroglucan as the rheology modifier in Ce:Zr Nitrate solution showed virtually no solution migration during drying up to temperatures of 100° C. Scleroglucan retained its viscosity and inhibited the solution from migrating in a very low pH environment.

Position #3 using xanthan gum showed signs of washcoat migration after several minutes of drying. The washcoat ultimately drained out to the bottom of the part and clogged the cells in the centre of the filter, although the initial viscosity for this position was lower than had been observed prior to the experimental run.

Position #4 with scleroglucan showed minimal washcoat migration after the core temperature of the filter increased during drying. Of the rheology modifiers tested, scleroglucan had the best gelling characteristics at increased temperatures in an acidic medium.

Position #5 using guar gum also showed good rheology characteristics during the drying cycle, although there was more washcoat migration during drying than for the #4 sample, the concentration of guar gum required for colloidal alumina slurries was significantly less than for scleroglucan.

EXAMPLE 6

Tolerance to pH and Multivalent Ions

Nitric acid was added to 600 g of deionised water to lower the pH to 1.2. 266 g of citric acid were then added, resulting in a pH of 1.03. 4.2 g of a commercially available xanthan gum (Vanzan®) were then successively dissolved in the solution. The resulting solution had a viscosity of 2000 cPs (measured by a Brookfield viscometer) and a pH of 1.05.

By contrast, 10.99 g of citric acid were added to 500 g of de-ionised water, followed by 44.26 g of palladium nitrate (13.759% palladium). The resulting pH was 1.1. 6.9 g of xanthan gum were then added. The solution did not thicken as the xanthan did not dissolve but formed a chunk precipitate.

What is claimed is:

1. A method of coating a substrate monolith comprising a first end face and a second end face and a plurality of substantially parallel channels extending from the first end face to the second end face with a washcoat composition, wherein the method comprises the steps of:
- (a) locating a containment means on top of the first end face of the substrate monolith;
- (b) dosing a predetermined quantity of a rheologically pseudoplastic washcoat composition comprising a liquid phase, at least one polysaccharide rheology modifier and either one or both of (i) and (ii), wherein (i) is a suspension of metal oxide particles into the containment means; and (ii) is at least one metal salt solute in the liquid phase, and wherein the order of steps (a) and (b) is (a) then (b) or (b) then (a);
- (c) applying pressure to the washcoat composition thereby to generate a shear stress in the washcoat composition and to transfer an entirety of the washcoat composition into the channels of the substrate monolith by plug flow, wherein the predetermined quantity of the washcoat composition is such that no more than 1 wt % of the predetermined quantity of the washcoat composition is drawn though the substrate monolith and expelled; and
- (d) rotating a part-coated substrate monolith resulting from step (c) so that the second end face is located at the top; and
- (e) repeating steps (a) to (c) inclusive without drying the part-coated substrate monolith.

2. A method according to claim 1, wherein a product of step (e) comprises a substrate monolith coated uniformly with a first layer of the washcoat composition.

3. A method according to claim 1, wherein the product of step (e) is subjected to a drying step.

4. A method according to claim 3, wherein the product of step (e) is coated with a second layer of the same or a different washcoat composition by repeating steps (a) to (e) inclusive.

5. A method according to claim 1, wherein the polysaccharide rheology modifier assumes a rod-like triple helical structure when dissolved in water.

6. A method according to claim 1, wherein the polysaccharide rheology modifier is Scleroglucan, Diutan gum or Welan gum.

* * * * *